US012691127B2

(12) United States Patent
Moraitis et al.

(10) Patent No.: US 12,691,127 B2
(45) Date of Patent: Jul. 28, 2026

(54) USE OF GLUCOCORTICOID RECEPTOR ANTAGONISTS IN COMBINATION WITH GLUCOCORTICOIDS TO TREAT ADRENAL INSUFFICIENCY

(71) Applicant: Corcept Therapeutics, Inc., Menlo Park, CA (US)

(72) Inventors: Andreas G. Moraitis, Menlo Park, CA (US); Pejman Cohan, Menlo Park, CA (US); Joseph K. Belanoff, Menlo Park, CA (US)

(73) Assignee: Corcept Therapeutics Incorporated, Redwood City, CA (US)

( * ) Notice: Subject to any disclaimer, the term of this patent is extended or adjusted under 35 U.S.C. 154(b) by 368 days.

(21) Appl. No.: 18/394,672

(22) Filed: Dec. 22, 2023

(65) Prior Publication Data

US 2024/0156835 A1 May 16, 2024

Related U.S. Application Data

(62) Division of application No. 17/525,409, filed on Nov. 12, 2021, now Pat. No. 11,890,289, which is a division of application No. 16/816,014, filed on Mar. 11, 2020, now Pat. No. 11,202,784, which is a division of application No. 15/565,291, filed as application No. PCT/US2016/024981 on Mar. 30, 2016, now Pat. No. 10,610,534.

(60) Provisional application No. 62/140,317, filed on Mar. 30, 2015.

(51) Int. Cl.
*A61K 31/567* (2006.01)
*A61K 31/437* (2006.01)
*A61K 31/473* (2006.01)
*A61K 31/513* (2006.01)
*A61K 31/575* (2006.01)

(52) U.S. Cl.
CPC .......... *A61K 31/567* (2013.01); *A61K 31/437* (2013.01); *A61K 31/473* (2013.01); *A61K 31/513* (2013.01); *A61K 31/575* (2013.01)

(58) Field of Classification Search
CPC .. A61K 31/567; A61K 31/437; A61K 31/473; A61K 31/513; A61K 31/575
See application file for complete search history.

(56) References Cited

U.S. PATENT DOCUMENTS

| | | | |
|---|---|---|---|
| 7,928,237 | B2 | 4/2011 | Clark et al. |
| 8,461,172 | B2 | 6/2013 | Clark et al. |
| 8,685,973 | B2 | 4/2014 | Clark et al. |
| 8,829,024 | B2 | 9/2014 | Belanoff et al. |
| 8,859,774 | B2 | 10/2014 | Hunt et al. |
| 9,273,047 | B2 | 3/2016 | Hunt et al. |
| 9,707,223 | B2 | 7/2017 | Hunt et al. |
| 10,610,534 | B2 | 4/2020 | Moraitis et al. |
| 11,202,784 | B2 | 12/2021 | Moraitis et al. |
| 2005/0037074 | A1 | 2/2005 | Ross et al. |
| 2010/0261693 | A1 | 10/2010 | Ulmann et al. |
| 2013/0012486 | A1 | 1/2013 | Belanoff et al. |
| 2014/0038926 | A1 | 2/2014 | Hunt et al. |
| 2014/0170768 | A1 | 6/2014 | Ehrenkranz |
| 2015/0148341 | A1 | 5/2015 | Hunt et al. |

FOREIGN PATENT DOCUMENTS

| | | | |
|---|---|---|---|
| EP | 0763541 | 7/1999 | |
| WO | 2004066920 | 8/2004 | |
| WO | 2004067529 | 8/2004 | |
| WO | 2005102271 | 11/2005 | |
| WO | WO-2012094618 A1 * | 7/2012 | .............. A61P 37/06 |
| WO | 2013177559 | 11/2013 | |

OTHER PUBLICATIONS

"KORLYM® FDA Label", Oct. 19, 2018, 21 pages.
U.S. Appl. No. 16/816,014 , "Advisory Action", Jun. 21, 2021, 3 pages.
U.S. Appl. No. 16/816,014 , "Final Office Action", Apr. 20, 2021, 11 pages.
U.S. Appl. No. 16/816,014 , "Non-Final Office Action", Dec. 15, 2020, 9 pages.
U.S. Appl. No. 16/816,014 , "Notice of Allowance", Oct. 14, 2021, 9 pages.
U.S. Appl. No. 17/525,409 , "Non-Final Office Action", Jul. 27, 2023, 10 pages.

(Continued)

*Primary Examiner* — Kamal A Saeed
*Assistant Examiner* — Quincy McKoy
(74) *Attorney, Agent, or Firm* — James Fox; Kilpatrick Townsend & Stockton LLP

(57) ABSTRACT

This invention provides for a method of treating secondary adrenal insufficiency by co-administrating therapeutically effective amounts of a glucocorticoid and a glucocorticoid receptor antagonist to the patient in need thereof. In some embodiments, the method includes the proviso that the patient not be otherwise in need of treatment with a glucocorticoid and a glucocorticoid receptor antagonist. The treatment method can increase the patient's morning or basal cortisol level to at least about 12 μg/dL or a standard control level, and in turn, expedite significantly the recovery of the HPA axis. The method provided herein can improve health outcomes and life-threatening complications associated with secondary adrenal insufficiency.

9 Claims, No Drawings

(56) References Cited

OTHER PUBLICATIONS

U.S. Appl. No. 17/525,409 , "Notice of Allowance", Dec. 8, 2023, 9 pages.
Canadian Patent Application No. 2,978,960 , "Office Action", Jun. 2, 2022, 4 pages.
Castinetti et al., "Medical Treatment of Cushing's Syndrome: Glucocorticoid Receptor Antagonists and Mifepristone", Neuroendocrinology, vol. 92, 2010, pp. 125-130.
Castinetti et al., "Merits and Pitfalls of Mifepristone in Cushing's Syndrome", European Journal of Endocrinology, vol. 160, No. 6, Jun. 2009, pp. 1003-1010.
Castinetti et al., "The Use of the Glucocorticoid Receptor Antagonist Mifepristone in Cushing's Syndrome", Neuroendocrinology, vol. 19, No. 4, Aug. 2012, pp. 295-299.
Chu et al., "Successful Long-Term Treatment of Refractory Cushing's Disease with High-Dose Mifepristone (RU 486)", The Journal of Clinical Endocrinology & Metabolism, vol. 86, No. 8, Aug. 2001, pp. 3568-3573.
Cui et al., "Perioperative Endocrine Therapy for Patients with Cushing's Syndrome Undergoing Retroperitoneal Laparoscopic Adrenalectomy", International Journal of Endocrinology, Clinical Study, vol. 12, 2012, 6 pages.
European Patent Application No. 16774094.3 , "Extended European Search Report", Oct. 30, 2018, 6 pages.
Fleseriu et al., "Mifepristone, a Glucocorticoid Receptor Antagonist, Produces Clinical and Metabolic Benefits in Patients with Cushing's Syndrome", The Journal of Clinical Endocrinology & Metabolism, vol. 97, No. 6, Mar. 30, 2012, pp. 2039-2049.
Gaillard et al., "Ru 486: A Steroid with Antiglucocorticosteroid Activity that Only Disinhibits the Human Pituitary-Adrenal System at a Specific Time of Day", Proceedings of the National Academy of Sciences of the United States of America, vol. 81, No. 12, Jun. 1984, pp. 3879-3882.
Gordon et al., "A Study of Hypothalamic-Pituitary-Adrenal Suppression Following Curative Surgery for Cushing's Syndrome Due to Adrenal Adenoma", European Journal of Endocrinology, vol. 114, No. 2, Feb. 1987, pp. 166-170.
Hopkins et al., "Exogenous Cushing's Syndrome and Glucocorticoid Withdrawal", Endocrinology Metabolism Clinics of North America, vol. 34, No. 2, Jun. 2005, pp. 371-384.
Ito et al., "Classification and Kinds of Side Effects That Can Be Predicted From Pharmacological Features,", Pharmacy, vol. 63, No. 2, 2012, pp. 273-277.
Johanssen et al., "Mifepristone (RU 486) in Cushing's Syndrome", European Journal of Endocrinology, vol. 157, No. 5, Nov. 2007, pp. 561-569.
Japanese Patent Application No. 2017-550837 , "Office Action", Nov. 7, 2019, 12 pages.
Japanese Patent Application No. 2020-018526 , "Office Action", Feb. 10, 2021, 2 pages.
Japanese Patent Application No. 2021-130694 , "Office Action", Jun. 2, 2022, 1 page.
Japanese Patent Application No. 2021-130694 , "Office Action", Dec. 16, 2022, 3 pages.
Keizer et al., "Mifepristone Treatment in Patients with Surgically Incurable Sphenoid-Ridge Meningioma: A Long-Term Follow-Up", Eye, vol. 18, No. 9, Mar. 19, 2004, pp. 954-958.
Laue et al., "Effect of Chronic Treatment with the Glucocorticoid Antagonist RIJ486 in Man: Toxicity, Immunological, and Hormonal Aspects", Journal of Clinical Endocrinology and Metabolism, vol. 71, No. 6, 1990, pp. 1474-1480.
PCT/US2016/024981 , "International Search Report and Written Opinion", Jun. 24, 2016, 15 pages.
Peppa et al., "Hypertension and Other Morbidities With Cushing's Syndrome Associated With Corticosteroids: a Review", Integrated Blood Pressure Control, vol. 4, Feb. 3, 2011, pp. 7-16.
Raux-Demay et al., "Transient Inhibition of RU 486 Antiglucocorticoid Action by Dexamethasone", The Journal of Clinical Endocrinology & Metabolism, vol. 70, No. 1, Jan. 1, 1990, pp. 230-233.
Sartor et al., "Mifepristone: Treatment of Cushing's Syndrome", Clinical Obstetrics, vol. 39, No. 2, 1996, pp. 506-510.
Schweitzer et al., "Clinical and Pharmacological Aspects of Accidental Triamcinolone Acetonide Overdosage: A Case Study", Netherlands Journal of Medicine, vol. 56, No. 1, 2000, pp. 12-16.
Singaporean Patent Application No. 11201707525T , "Further Written Opinion", Oct. 4, 2021.
Singaporean Patent Application No. 11201707525T , "Written Opinion", Oct. 25, 2018, 10 pages.
Suzuki et al., "Hypercalcemia in Glucocorticoid Withdrawal", Endocrinol. Japon., vol. 33, No. 2, 1986, pp. 203-209.
Utz et al., "Pituitary Surgery and Postoperative Management in Cushing's Disease", Endocrinology and Metabolism Clinics of North America, vol. 34, Issue 2, 2005, pp. 459-478.

* cited by examiner

USE OF GLUCOCORTICOID RECEPTOR ANTAGONISTS IN COMBINATION WITH GLUCOCORTICOIDS TO TREAT ADRENAL INSUFFICIENCY

CROSS-REFERENCES TO RELATED APPLICATIONS

This application is a U.S. Divisional Patent Application of U.S. patent application Ser. No. 17/525,409, filed Nov. 12, 2021, which is a U.S. Divisional Patent Application of U.S. patent application Ser. No. 16/816,014, filed Mar. 11, 2020, (now U.S. Pat. No. 11,202,784, issued Dec. 21, 2021), which is a U.S. Divisional Patent Application of U.S. patent application Ser. No. 15/565,291, filed Oct. 9, 2017, (now U.S. Pat. No. 10,610,534, issued Apr. 7, 2020), which is a U.S. National Phase entry under 35 U.S.C. § 371 of International Application No. PCT/US2016/024981, filed Mar. 30, 2016, which claims priority to U.S. Provisional Application No. 62/140,317, filed Mar. 30, 2015, the disclosures of which are hereby incorporated by reference in their entireties for all purposes.

BACKGROUND OF THE INVENTION

Adrenal insufficiency is an endocrine disorder that occurs when the adrenal glands do not produce adequate amounts of steroid hormones, such as cortisol. Primary adrenal insufficiency occurs when the adrenal glands are either destroyed or absent. Secondary adrenal insufficiency occurs when the adrenal glands are intact, but are not stimulated to produce cortisol due to the absence or low levels of adrenocorticotropic hormone (ACTH).

ACTH is a polypeptide-based hormone that is normally produced and secreted by the anterior pituitary gland. ACTH stimulates secretion of cortisol and other glucocorticoids (GCs) by specialized cells of the adrenal cortex. In healthy mammals, ACTH secretion is tightly regulated. ACTH secretion is positively regulated by corticotropin releasing hormone (CRH), which is released by the hypothalamus. ACTH secretion is negatively regulated by cortisol and other glucocorticoids. A disruption to the tightly regulated hypothalamus-pituitary-adrenal gland (HPA) axis can cause low levels of ACTH, and in turn, secondary adrenal insufficiency.

Low ACTH secretion generally results from prolonged exposure to glucocorticoid drugs, or conditions that cause a total absence of ACTH or a suppression of ACTH production/secretion. Such conditions include pituitary tumors, craniopharyngiomas, radiation therapy to the pituitary, cysts in the pituitary, some inflammatory diseases, and surgical removal of ACTH-secreting and cortisol-secreting tumors. Patients with pituitary ACTH-secreting tumors (Cushing's Disease) and patient with non-pituitary ACTH- and cortisol-secreting tumors (Cushing's Syndrome) can be treated by tumor resection. Removal of the tumor is invariably followed by secondary adrenal insufficiency, and the need for glucocorticoid replacement therapy.

The most common cause of secondary adrenal insufficiency is the use of long-term glucocorticoid (GC) replacement therapy which is used to treat numerous diseases and disorders. For instance, glucocorticoids, such as prednisone, cortisone, methylprednisolone, hydrocortisone, and dexamethasone, are recommending for treating rheumatoid arthritis, systemic lupus erythematosus, Sjögren's syndrome, ulcerative colitis, inflammatory bowel disease, chronic obstructive pulmonary disease, psoriasis, systemic vasculitis, myositis, asthma, allergic rhinitis, other allergies, skin conditions, inflammatory diseases, etc. Synthetic glucocorticoids are steroid hormones that mimic the function of cortisol, and thus reduce endogenous cortisol levels. The pituitary recognizes glucocorticoids as cortisol, and thus produces lower levels of ACTH. ACTH suppression, in turn, reduces endogenous cortisol production/secretion. When glucocorticoids are withdrawn and the HPA axis fails to produce adequate levels of ACTH, secondary adrenal insufficiency can occur. Adrenal insufficiency originates from the suppression of the hypothalamic CRH producing cells by chronic glucocorticoid excess which consequently impairs pituitary-adrenal function. In addition, glucocorticoids inhibit the secretion of stored ACTH and repress the transcription of the POMC gene, which encodes the peptide ACTH. In exogenous Cushing's syndrome, the length and dose of glucocorticoid exposure are independent predictors of recovery of adrenal function.

Secondary adrenal insufficiency is currently treated with glucocorticoid drugs to substitute for cortisol until the HPA axis recovers to restore ACTH and cortisol to normal levels. The time-limiting step for HPA recovery appears to be the CRH producing neurons of the hypothalamus. Unfortunately, glucocorticoid replacement therapy can prolong the recovery of the HPA axis when a high dose is used or if the timing of GC administration is inappropriate (e.g., when it is given every 8 or 12 hours). The main risk for patients with secondary adrenal insufficiency is poor response to GC therapy. As such, novel and efficacious pharmacotherapies that are needed to promote recovery of the HPA axis in patients with secondary adrenal insufficiency.

BRIEF SUMMARY OF THE INVENTION

In one aspect, the present invention provides a method for treating a patient suspected of having secondary adrenal insufficiency. In some embodiments, the patient has secondary adrenal insufficiency. The method comprises co-administering a therapeutically effective amount of a glucocorticoid (GC) and a glucocorticoid receptor antagonist (GRA) to a patient in need thereof to increase the patient's morning plasma level of cortisol to at least about 12 μg/dL or a standard control level. In some cases, the patient's morning plasma level of cortisol increased to about 12 μg/dL, about 13 μg/dL, about 14 μg/dL, about 15 μg/dL, about 16 μg/dL, about 17 μg/dL, about 18 μg/dL, about 19 μg/dL, about 20 μg/dL, about 21 μg/dL, about 22 μg/dL, about 23 μg/dL, about 24 μg/dL, about 25 μg/dL, or more. In some embodiments, if the patient suffering from secondary insufficiency has a cortisol level below 12 μg/dL, e.g., from about 5 μg/dL to about 11.9 μg/dL, administration of GC and GRA can increase the patient's cortisol level to about 18 μg/dL or more, e.g., 18 μg/dL, about 19 μg/dL, about 20 μg/dL, about 21 μg/dL, about 22 μg/dL, about 23 μg/dL, about 24 μg/dL, about 25 μg/dL, or more, after ACTH administration (Cosyntropin stimulation test). In some embodiments, the subject is not otherwise in need of a combination treatment with a glucocorticoid and glucocorticoid receptor antagonist.

In some embodiments, the patient is suspected of having secondary adrenal insufficiency due to exogenous Cushing's syndrome (e.g., due to prolonged use of a glucocorticoid). In other embodiments, the patient is suspected of having secondary adrenal insufficiency after surgery for endogenous Cushing's syndrome. In some cases, the patient is suspected of having secondary adrenal insufficiency after successful surgery of a pituitary ACTH secreting tumor. In other cases, the patient is suspected of having secondary adrenal insufficiency after successful surgery for an extra-adrenal cortisol secreting tumor (e.g., ovarian cancer). In some cases, the patient is suspected of having secondary adrenal insufficiency after successful surgery for a unilateral hyperplastic adrenal gland associated with autonomous cortisol secretion. For example, the patient can have secondary adrenal insufficiency after successful surgery for an ectopic ACTH secreting non pituitary tumor. In another case, the patient can have secondary adrenal insufficiency after successful surgery for a unilateral adrenocortical cortisol secreting tumor.

In some embodiments, the patient has not received glucocorticoids and glucocorticoid receptor antagonist treatment (e.g., GCs or GRAs in combination with GCs). In some instances, the patient has not received glucocorticoids and glucocorticoid receptor antagonist treatment (e.g., GCs or GRAs in combination with GCs) to treat a disorder or condition selected from the group consisting of glaucoma, inflammatory diseases, rheumatoid arthritis, asthma and rhinitis, chronic pulmonary disease, allergies, and autoimmune diseases. In some cases the patient has not received glucocorticoids and glucocorticoid receptor antagonist treatment (e.g., GCs or GRAs in combination with GCs) to reduce a side effect of glucocorticoid treatment. For instance, the side effect can be weight gain, glaucoma, fluid retention, increased blood pressure, mood swings, cataracts, high blood sugar, diabetes, infection, loss of calcium from bones, osteoporosis, menstrual irregularities, fat redistribution, growth retardation, cushingoid appearance, or any combination thereof.

In some cases, the glucocorticoid receptor antagonist is a selective inhibitor of the glucocorticoid receptor. In some embodiments, the glucocorticoid receptor antagonist comprises a steroidal backbone with at least one phenyl-containing moiety in the 11-β position of the steroidal backbone. In some cases, the phenyl-containing moiety in the 11-β position of the steroidal backbone is a dimethylaminophenyl moiety. In some cases, the glucocorticoid receptor antagonist is mifepristone. In some embodiments, the glucocorticoid receptor antagonist is selected from the group consisting of 11β-(4-dimethylaminoethoxyphenyl)-17α-propynyl-17β-hydroxy-4,9 estradien-3-one and (17α)-17-hydroxy-19-(4-methylphenyl)androsta-4,9(11)-dien-3-one. In some embodiments, the glucocorticoid receptor antagonist is (11β, 17β)-11-(1,3-benzodioxol-5-yl)-17-hydroxy-17-(1-propynyl)estra-4,9-dien-3-one.

In some embodiments, the glucocorticoid receptor antagonist has a non-steroidal backbone. In some cases, the glucocorticoid receptor antagonist backbone is a cyclohexyl pyrimidine. In some cases, wherein the cyclohexyl pyrimidine has the following formula:

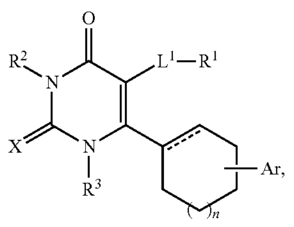

wherein the dashed line is absent or a bond; X is selected from the group consisting of O and S; $R^1$ is selected from the group consisting of cycloalkyl, heterocycloalkyl, aryl and heteroaryl, optionally substituted with from 1 to 3 $R^{1a}$ groups; each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl $OR^{1b}$, halogen, $C_{1-6}$ haloalkyl, $C_{1-6}$ haloaloxy, $OR^{1b}$, $NR^{1b}R^{1c}$ $C(O)R^{1b}$, $C(O)OR^{1b}$, $OC(O)R^{1b}$, $C(O)NR^{1b}R^{1c}$, $NR^{1b}C(O)R^{1c}$, $SO_2R^{1b}$, $SO_2NR^{1b}R^{1c}$, cycloalkyl, heterocycloalkyl, aryl and heteroaryl; $R^{1b}$ and $R^{1c}$ are each independently selected from the group consisting of H and $C_{1-6}$ alkyl; $R^2$ is selected from the group consisting of H, $C_{1-6}$ alkyl, $C_{1-6}$ alkyl-$OR^{1b}$, $C_{1-6}$ alkyl $NR^{1b}R^{1c}$ and $C_{1-6}$ alkylene heterocycloalkyl; $R^3$ is selected from the group consisting of H and $C_{1-6}$ alkyl; Ar is aryl, optionally substituted with 1-4 $R^4$ groups; each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy; $L^1$ is a bond or $C_{1-6}$ alkylene; and subscript n is an integer from 0 to 3, or salts and isomers thereof.

In some cases, the glucocorticoid receptor antagonist backbone is a fused azadecalin. In some cases, the fused azadecalin is a compound having the following formula:

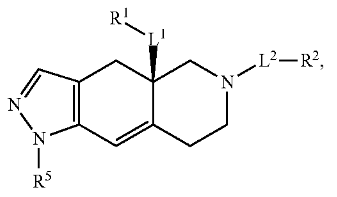

wherein $L^1$ and $L^2$ are members independently selected from a bond and unsubstituted alkylene; $R^1$ is a member selected from unsubstituted alkyl, unsubstituted heteroalkyl, unsubstituted heterocycloalkyl, —$OR^{1A}$, $NR^{1C}R^{1D}$, —$C(O)NR^{1C}R^{1D}$ and —$C(O)OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen; $R^2$ has the formula:

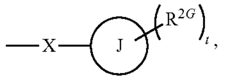

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$; J is phenyl; t is an integer from 0 to 5; X is —$S(O_2)$—; and $R^5$ is phenyl optionally substituted with 1-5 $R^{5A}$ groups, wherein $R^{5A}$ is a member selected from hydrogen, halogen, —$OR^{5A1}$, $S(O_2)NR^{5A2}R^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

In some cases, the glucocorticoid receptor antagonist backbone is a heteroaryl ketone fused azadecalin or an octahydro fused azadecalin. In some cases, the heteroaryl ketone fused azadecalin has the formula:

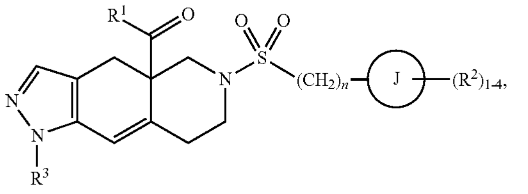

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, CN, N-oxide, $C_{3-8}$ cycloalkyl, and $C_{3-8}$ heterocycloalkyl; ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups; alternatively, two $R^2$ groups linked to the same carbon are combined to form an oxo group (=O); alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups; $R^{2a}$ and $R^{2b}$ are each independently selected from the group consisting of hydrogen and $C_{1-6}$ alkyl; each $R^{2c}$ is independently selected from the group consisting of hydrogen, halogen, hydroxy, $C_{1-6}$ alkoxy, $C_{1-6}$ haloalkoxy, CN, and $NR^{2a}R^{2b}$; each $R^{2d}$ is independently selected from the group consisting of hydrogen and $C_{1-6}$ alkyl, or two $R^{2d}$ groups attached to the same ring atom are combined to form (=O); $R^3$ is selected from the group consisting of phenyl and pyridyl, each optionally substituted with 1-4 $R^{3a}$ groups; each $R^{3a}$ is independently selected from the group consisting of hydrogen, halogen, and $C_{1-6}$ haloalkyl; and subscript n is an integer from 0 to 3; or salts and isomers thereof.

In some cases, the octahydro fused azadecalin has the formula:

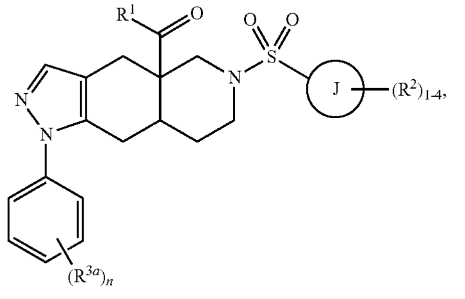

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$; each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl; ring J is selected from the group consisting of an aryl ring and a heteroaryl ring having from 5 to 6 ring members and from 1 to 4 heteroatoms each independently selected from the group consisting of N, O and S; each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, CN, OH, $NR^{2a}R^{2b}$, $C(O)R^{2a}$, $C(O)OR^{2a}$, $C(O)NR^{2a}R^{2b}$, $SR^{2a}$, $S(O)R^{2a}$, $S(O)_2R^{2a}$, $C_{3-8}$ cycloalkyl, and $C_{3-8}$ heterocycloalkyl having from 1 to 3 heteroatoms each independently selected from the group consisting of N, O and S; alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups; $R^{2a}$, $R^{2b}$ and $R^{2c}$ are each independently selected from the group consisting of hydrogen and $C_{1-6}$ alkyl; each $R^{3a}$ is independently halogen; and subscript n is an integer from 0 to 3, or salts and isomers thereof.

In some embodiments, the glucocorticoid is selected from the group consisting of hydrocortisone, prednisone, dexamethasone, a glucocorticoid analogue, a synthetic glucocorticoid analogue, a glucocorticoid receptor agonist, and derivatives thereof.

In some embodiments, the patient has been administered an exogenous glucocorticoid for a long period of time. In some cases, the long period of time is at least three weeks, e.g., 3 weeks, 4 weeks, 1 month, 2 months, 3 months, 4 months, 5 months, 6 months, 7 months, 8 months, 9 months, 10 months, 11 months, 12 months, 1.5 years, 2 years, 3 years or more. In some cases, the exogenous glucocorticoid is prednisone, prednisolone, hydrocortisone, dexamethasone, or a combination thereof.

Other objects, features, and advantages of the present invention will be apparent to one of skill in the art from the following detailed description and FIGURES.

DETAILED DESCRIPTION OF THE INVENTION

I. Introduction

The invention provides a novel treatment method for treating secondary adrenal insufficiency in a subject in need thereof by administering therapeutically effective amounts of a glucocorticoid receptor antagonist (GRA) and a glucocorticoid (GC). Administration of this combination treatment can promote the production and/or secretion of cortisol such that the subject's morning cortisol level in plasma is at least about 12 μg/dL or a standard control level. In some embodiments, the method includes the proviso that the patient is not otherwise in need of administration with a GC and GRA for treatment of glaucoma, inflammatory diseases, rheumatoid arthritis, asthma and rhinitis, chronic obstructive pulmonary disease, allergies and autoimmune diseases. In some embodiments, the method also includes the proviso that the patient is not otherwise in need of combination treatment with a GC and GRA for the reduction of a side effect of GC monotreatment, such as weight gain, glaucoma, fluid retention, increased blood pressure, mood swings, cataracts, high blood sugar, diabetes, infection, loss of calcium from bones, osteoporosis, menstrual irregularities, fat redistribution, growth retardation and cushingoid appearance.

II. Definitions

As used herein, the following terms have the meanings ascribed to them unless specified otherwise. The abbreviations used herein have their conventional meaning within the chemical and biological arts.

The term "secondary adrenal insufficiency" refers to a condition in which the adrenal glands do not produce adequate amounts of cortisol due to a lack of adrenocorticotrophic hormone (ACTH). Unlike patients with primary adrenal insufficiency, those with secondary adrenal insufficiency produce substantially normal levels of aldosterone and have at least one intact adrenal gland. Secondary adrenal insufficiency is common in patients given long-term glucocorticoid-replacement therapy.

The term "Cushing's syndrome" refers to a disease caused by prolonged exposure to endogenous or exogenous glucocorticoids. Symptoms of Cushing's syndrome include, but are not limited to one or more of the following: weight gain, high blood pressure, poor short term memory, poor concentration, irritability, excess hair growth, impaired immunological function, ruddy complexion, extra fat in the neck region, moon face, fatigue, red stretch marks, irregular menstruation, or a combination thereof. Symptoms of Cushing's syndrome can additionally or alternatively include without limitation one or more of the following: insomnia, recurrent infection, thin skin, easy bruising, weak bones, acne, balding, depression, hip or shoulder weakness, swelling of the extremities, diabetes mellitus, elevated white blood cell count, hypokalemic metabolic alkalosis, or a combination thereof.

The term "endogenous Cushing's syndrome" refers to a type of Cushing's syndrome caused by, for example, endogenous overproduction of cortisol by a pituitary ACTH-secreting tumor (Cushing's disease), a non-pituitary ACTH-secreting tumor, or a cortisol-secreting tumor (adrenal or extra-adrenal). An ACTH-secreting tumor can be pituitary adenomas, pituitary adenocarcinomas, carincinoid tumors and neuroendocrine tumors Cortisol-secreting tumors include, and are not limited to, cortisol producing adrenal adenomas, adrenocortical carcinomas, primary pigmented micronodular adrenal disease (PPNAD), ACTH independent macronodular adrenal hyperplasia (AIMAH), and extra-adrenal cortisol secreting tumors, e.g., ovarian carcinomas.

The term "exogenous Cushing's syndrome" refers to a type of Cushing's syndrome caused by repeated or prolonged administration of synthetic glucocorticoids, such as prednisone, hydrocortisone, dexamethasone and the like. Subjects receiving long-term steroid replacement therapy, exhibiting symptoms or signs of Cushing's syndrome, and having low serum cortisol levels may have exogenous Cushing's syndrome. A standard reference range for low serum cortisol level is <about 4 μg/dL in the morning.

"Treat," "treating" and "treatment" refer to any indicia of success in the treatment or amelioration of a pathology or condition, including any objective or subjective parameter such as abatement; remission; diminishing of symptoms or making the pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters; including the results of a physical examination; histopathological examination (e.g., analysis of biopsied tissue); laboratory analysis of urine, saliva, an inferior petrosal sinus sample, serum, plasma, or blood (e.g., to detect cortisol or adrenocorticotropic hormone levels); or imaging (e.g., imaging of detectably labeled octreotide). Effective treatment can refer to an increase in cortisol and/or adrenocorticotropic hormone in a subject's body.

"Patient" or "subject in need thereof" refers to a person having, or suspected of having, a secondary adrenal insufficiency.

As used herein, the term "simultaneously administering or sequentially administering" or "coadministering", as used interchangeably, refers to administration of a GRA compound and glucocorticoid (GC) such that the two compounds are in the body at the same time in amounts effective to treat a secondary adrenal insufficiency.

As used herein, the term "effective amount," "amounts effective," or "therapeutically effective amount" refers to an amount or amounts of one or more pharmacological agents effective to treat, eliminate, or mitigate at least one symptom of the disease being treated. In some cases, "effective amount," "amounts effective," or "therapeutically effective amount" can refer to an amount of a functional agent or of a pharmaceutical composition useful for exhibiting a detectable therapeutic or inhibitory effect. The effect can be detected by any assay method known in the art. In some cases, the amounts effective, or the like, refer to amounts effective to increase ACTH levels or cortisol (e.g., plasma cortisol, serum cortisol, salivary cortisol, or urinary free cortisol) levels. In some cases, the amounts effective, or the like, refer to amounts effective to increase ACTH levels or cortisol levels, or a combination thereof, by at least 10%, 20%, 30%, 40%, 50%, 60%, 75%, 90%, 99%, or more.

The term "morning plasma level of cortisol" refers to a level, amount or concentration of cortisol in plasma in the morning, e.g., between about 7 a.m. to about 9 a.m. To measure a patient's morning plasma level of cortisol, samples are drawn from the patient with normal circadian rhythms (e.g., a nighttime sleep cycle) between 7 a.m. and 9 a.m. The normal range of serum cortisol in the morning is about 4 μg/dL to about 28 μg/dL. To convert from μg/dL cortisol to nmol/L cortisol, multiply by the cortisol conversion factor (27.59).

The term "standard control level," in the context of a plasma cortisol level, refers to a level, amount or concentration of cortisol as determined in a control individual, such as a healthy individual, an individual who does not have secondary adrenal insufficiency. In some instances, a standard control level is an average standard control level determined from a control population of individuals, e.g., a population of healthy, normal individuals. In some embodiments, these individuals are within the appropriate parameters, if applicable, for the purpose of screening for and/or monitoring for secondary adrenal insufficiency using the methods of the present disclosure. Optionally, the individuals are of similar age or similar ethnic background. The status of the selected individuals can be confirmed by well established, routinely employed methods including but not limited to general physical examination of the individuals and general review of their medical history.

The phrase "prolonged use of a glucocorticoid" refers to the administration of one glucocorticoid drug to a patient for the treatment of a disease or disorder wherein the patient receives the glucocorticoid drug for a period of time, for example, at least three weeks or more. In some cases, the patient receives a high dose of glucocorticoid drug and undergoes drug tapering (gradual withdrawl or discontinuation of the drug) before the drug treatment is stopped.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

"Glucocorticoid" ("GC") refers to a steroid hormone that binds to a glucocorticoid receptor. Glucocorticoids are typically characterized by having 21 carbon atoms, an α,β-unsaturated ketone in ring A, and an α-ketol group attached to ring D. They differ in the extent of oxygenation or hydroxylation at C-11, C-17 and C-19 (Rawn, "Biosynthesis and Transport of Membrane Lipids and Formation of Cholesterol Derivatives," in Biochemistry, Daisy et al. (eds.), 1989, pg. 567). The term "glucocorticoid" includes any compound known in the art that is referred to as a glucocorticoid receptor agonist, glucocorticoid, glucocorticosteroid, corticoid, corticosteroid, or steroid that binds to and activates a glucocorticoid receptor.

"Glucocorticoid receptor" ("GR") refers to the type II GR which specifically binds to cortisol and/or cortisol analogs such as dexamethasone (See, e.g., Turner & Muller, *J Mol Endocrinol,* 2005 35 283-292). The GR is also referred to as the cortisol receptor. The term includes isoforms of GR, recombinant GR and mutated GR. Inhibition constants ($K_i$) against the human GR receptor type II (Genbank: P04150) are between 0.0001 nM to 1,000 nM; preferably between 0.0005 nM to 10 nM, and most preferably between 0.001 nM to 1 nM.

The term "glucocorticoid receptor antagonist" or "GRA" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," the drug preferentially binds to the GR rather than other nuclear receptors, such as mineralocorticoid receptor (MR), androgen receptor (AR), or progesterone receptor (PR). It is preferred that the specific glucocorticoid receptor antagonist bind GR with an affinity that is 10× greater ($1/10^{th}$ the $K_d$ value) than its affinity to the MR, AR, or PR, both the MR and PR, both the MR and AR, both the AR and PR, or to the MR, AR, and PR. In a more preferred embodiment, the specific glucocorticoid receptor antagonist binds GR with an affinity that is 100× greater ($1/100^{th}$ the $K_d$ value) than its affinity to the MR, AR, or PR, both the MR and PR, both the MR and AR, both the AR and PR, or to the MR, AR, and PR.

The term "selective inhibitor" in the context of glucocorticoid receptor, refers to a chemical compound that selectively interferes with the binding a specific glucocorticoid receptor agonist and a glucocorticoid receptor.

The term "steroidal backbone" in the context of glucocorticoid receptor antagonists containing such refers to glucocorticoid receptor antagonists that contain modifications of the basic structure of cortisol, an endogenous steroidal glucocorticoid receptor ligand. The basic structure of a steroidal backbone is provided as Formula I:

Formula I

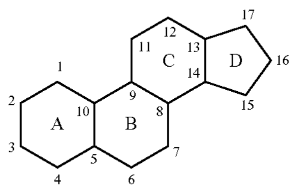

Steroidal Backbone

The two most commonly known classes of structural modifications of the cortisol steroid backbone to create glucocorticoid antagonists include modifications of the 11-β hydroxy group and modification of the 17-β side chain (See, e. g., Lefebvre (1989) J. Steroid Biochem. 33: 557-563).

As used herein, the phrase "non-steroidal backbone" in the context of glucocorticoid receptor antagonists containing such refers to glucocorticoid receptor antagonists that do not share structural homology to, or are not modifications of, cortisol. Such compounds include synthetic mimetics and analogs of proteins, including partially peptidic, pseudopeptidic and non-peptidic molecular entities.

Non-steroidal GRA compounds also include glucocorticoid receptor antagonists having a cyclohexyl-pyrimidine backbone, a fused azadecalin backbone, a heteroaryl ketone fused azadecalin backbone, or an octahydro fused azadecalin backbone. Exemplary glucocorticoid receptor antagonists having a cyclohexyl-pyrimidine backbone include those described in U.S. Pat. No. 8,685,973. Exemplary glucocorticoid receptor antagonists having a fused azadecalin backbone include those described in U.S. Pat. Nos. 7,928,237; and 8,461,172. Exemplary glucocorticoid receptor antagonists having a heteroaryl ketone fused azadecalin backbone include those described in U.S. 2014/0038926. Exemplary glucocorticoid receptor antagonists having an octohydro fused azadecalin backbone include those described in U.S. Provisional Patent Appl. No. 61/908,333, entitled Octahydro Fused Azadecalin Glucocorticoid Receptor Modulators, filed on Nov. 25, 2013.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc.

"Alkoxy" refers to an alkyl group having an oxygen atom that connects the alkyl group to the point of attachment: alkyl-O—. As for the alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Halogen" refers to fluorine, chlorine, bromine and iodine.

"Haloalkyl" refers to alkyl, as defined above, where some or all of the hydrogen atoms are replaced with halogen atoms. As for the alkyl group, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethane includes 1,1,1-trifluoromethyl.

"Haloalkoxy" refers to an alkoxy group where some or all of the hydrogen atoms are substituted with halogen atoms. As for the alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2-trifluoroethoxy, perfluoroethoxy, etc.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —$S(O)_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxalidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, N-oxide, —S(O)— and —$S(O)_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring heteroatoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heteroatoms" refers to O, S or N.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Isomers" refers to compounds with the same chemical formula but which are structurally distinguishable.

"Tautomer" refers to one of two or more structural isomers which exist in equilibrium and which are readily converted from one form to another.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Detailed Description of Embodiments

The present invention provides a method of treating secondary adrenal insufficiency in a subject in need thereof. In one aspect, a subject suffering from secondary adrenal insufficiency is administered simultaneously or sequentially therapeutically effective amounts of a GC and a GRA, such that the subject's plasma cortisol level in the morning (i.e., anytime from 7 a.m. to 9 a.m.) increases at least 12 μg/dL, e.g., 12 μg/dL, 13 μg/dL, 14 μg/dL, 15 μg/dL, 16 μg/dL, 17 μg/dL, 18 μg/dL, 19 μg/dL, 20 μg/dL, 21 μg/dL, 22 μg/dL, or more. In some instances, the subject has undergone treatment for endogenous Cushing's syndrome. In other instances, the subject has exogenous Cushing's syndrome. In another case, the subject has been administered an exogenous glucocorticoid for a long period of time.

A. Subjects with Secondary Adrenal Insufficiency

Secondary adrenal insufficiency involves ACTH deficiency which may be due to an abnormally functioning or damaged pituitary gland or hypothalamus. ACTH deficiency leads to insufficient cortisol production. Unlike in primary adrenal insufficiency, the adrenal glands in patients with secondary adrenal insufficiency are intact and produce normal amounts of aldosterone. Symptoms of secondary adrenal insufficiency include dizziness, fatigue, muscle weakness, weight loss, decreased or loss of appetite, nausea, vomiting, diarrhea, depression, irritability, muscle, joint, abdominal or back pain, loss of hair, headache and sweating.

Secondary adrenal insufficiency can occur in patients receiving a pro-longed glucocorticoid therapy, such as synthetic glucocorticoid (e.g., prednisone, hydrocortisone, dexamethasone, cortisone) therapy. This condition is referred to as exogenous Cushing's syndrome. When receiving glucocorticoids for a long time (e.g., at least three weeks or more), the patient's adrenal glands may produce low or undetectable levels of cortisol. Patients with exogenous Cushing's syndrome can have low ACTH levels, low cortisol levels, and no response to a low dose ACTH stimulation test. Treatment of exogenous Cushing's syndrome includes slowly withdrawing the glucocorticoid to reverse the effects of the impaired adrenal gland. The method described herein can promote or accelerate the repair of the patient's HPA axis such that the adrenal glands secrete cortisol at normal, healthy levels.

Secondary adrenal insufficiency can also arise in patients with endogenous Cushing's syndrome after surgical removal of an ACTH-secreting tumor or a cortisol-secreting tumor in, for example, an adrenal gland. Endogenous Cushing's syndrome is caused by ACTH-secreting tumors or cortisol-secreting tumors, e.g., cortisol producing adrenal adenomas, adrenocortical carcinomas, primary pigmented micronodular adrenal disease (PPNAD), ACTH independent macronodular adrenal hyperplasia (AIMAH), extraadrenal cortisol secreting tumors, e.g., ovarian carcinomas, adrenal adenomas, micronodular hyperplasia, adrenal carcinomas, pituitary adenomas, pituitary adenocarcinomas, carincinoid tumors, neuroendocrine tumors, or combinations thereof. Treatment of endogenous Cushing's syndrome includes administration of a therapeutic drug, e.g., aminoglutethimide (Cytadren®), and mitotane (Lysodren), and/or surgery. Surgical removal of the ACTH-secreting tumor or cortisol-secreting tumor is invariably followed by secondary adrenal insufficiency and the need for glucocorticoid replacement therapy. The duration of secondary adrenal insufficiency can vary and glucocorticoid replacement therapy is maintained until the adrenal function recovers to normal, healthy function. The methods provided herein can significantly expedite the recovery of the patient's HPA axis.

In cases when secondary adrenal insufficiency is due to a structural pituitary or hypothalamic abnormality (e.g., patients with hypophysectomy, patients with pituitary apoplexy, or any other condition leading to destruction of those glands), the methods of the present invention may not be useful. Administration of a GRA and a GC requires an anatomically intact hypothalamus and pituitary, or at least the part of those glands involved in the regulation and production of CRH and ACTH should be intact.

Generally, a clinician diagnoses secondary adrenal insufficiency in patients presenting with one or more symptoms of the disorder by evaluating the patient's medical history. Further diagnostic testing may not be needed if the patient has had complete removal of a pituitary or hypothalamus tumor. If the patient has had partial surgery of the pituitary, hypothalamus or adrenal glands, or is suspected of having ACTH deficiency, further diagnostic assays to detect cortisol levels may be performed.

Non-limiting examples of such diagnostic or detection assays include the low dose ACTH stimulation test, corticotropin-releasing hormone (CRH) stimulation test, low-dose dexamethasone test, assays to detect total and/or free cortisol levels in, for example, serum, plasma, saliva, urine, or feces, and assays to detect ACTH levels. In the low dose ACTH stimulation test, levels of ACTH and cortisol are measured before administration of the synthetic derivative of ACTH (cosyntropin, Cortrosyn®). A second cortisol measurement is taken one hour later. If the level of cortisol remains substantially unchanged or is less than about 17 μg/dL after administration of cosyntropin, secondary adrenal insufficiency may be indicated. The patient's adrenal glands may be evaluated by CT scan to detect abnormal size or possible impairment. In some cases, a CT scan or MRI of the brain is performed to assess the presence of a pituitary tumor or atrophy.

Patients with secondary adrenal insufficiency have lower than normal levels of cortisol in the morning. For example, such a patient may have a serum cortisol level of less than 4 μg/dL between 7 a.m. to 9 a.m. In some embodiments, the method disclosed herein is useful to treat a patient with secondary adrenal insufficiency and a basal cortisol (e.g., basal total cortisol or basal free cortisol) level of less than 12 μg/dL, e.g., 11.5 μg/dL, 11 μg/dL, 10 μg/dL, 9 μg/dL, 8 μg/dL, 7 μg/dL, 6 μg/dL, 5 μg/dL, 4 μg/dL, 3 μg/dL, 2 μg/dL, 1 μg/dL, or less than 1 μg/dL. A patient's basal cortisol level can be measured in plasma, serum, saliva, urine, and the like. In some instances, a patient with secondary adrenal insufficiency has a basal plasma or serum cortisol level of less than 12 μg/dL, e.g., 11.5 μg/dL, 11 μg/dL, 10 μg/dL, 9 μg/dL, 8 μg/dL, 7 μg/dL, 6 μg/dL, 5 μg/dL, 4 μg/dL, 3 μg/dL, 2 μg/dL, 1 μg/dL, or less than 1 μg/dL.

In some aspects of the present disclosure, the patient is not being administered a combination treatment comprising a GRA and a GC. In other words, the patient is treatment naïve. In some embodiments, the patient receiving a therapeutically effective amount of a GRA in combination with a GC, according to the methods described herein, is not been treated for a disorder or condition selected from the group consisting of glaucoma, inflammatory diseases, rheumatoid arthritis, asthma and rhinitis, chronic pulmonary disease, allergies, and autoimmune diseases. In other embodiments, the patient is not receiving a therapeutically effective amount of a GRA in combination with a therapeutically effective amount of a GC to reduce one or more side effects of glucocorticoid treatment. The side effects can be of weight gain, glaucoma, fluid retention, increased blood pressure, mood swings, cataracts, high blood sugar, diabetes, infection, loss of calcium from bones, osteoporosis, menstrual irregularities, fat redistribution, growth retardation, cushingoid appearance, or any combination thereof.

The methods disclosed herein can be used to treat a patient with secondary adrenal insufficiency, with the proviso that the patient not be otherwise in need of treatment with a combination treatment of a glucocorticoid receptor antagonist and a glucocorticoid.

B. Glucocorticoid Receptor Antagonists

The methods of the present invention generally provide administering a glucocorticoid receptor antagonist. In some cases, the glucocorticoid receptor antagonist is a specific glucocorticoid receptor antagonist. As used herein, a specific glucocorticoid receptor antagonist refers to a composition or compound which inhibits any biological response associated with the binding of a glucocorticoid receptor to an agonist by preferentially binding to the glucocorticoid receptor rather than another nuclear receptor (NR). In some embodiments, the specific glucocorticoid receptor antagonist binds preferentially to glucocorticoid receptor rather than the mineralocorticoid receptor (MR), androgen receptor (AR), or progesterone receptor (PR). In an exemplary embodiment, the specific glucocorticoid receptor antagonist binds preferentially to glucocorticoid receptor rather than the mineralocorticoid receptor (MR). In another exemplary embodiment, the specific glucocorticoid receptor antagonist binds preferentially to glucocorticoid receptor rather than the progesterone receptor (PR). In another exemplary embodiment, the specific glucocorticoid receptor antagonist binds preferentially to glucocorticoid receptor rather than the androgen receptor (AR). In yet another exemplary embodiment, the specific glucocorticoid receptor antagonist binds preferentially to glucocorticoid receptor in comparison to MR and PR, MR and AR, PR and AR, or MR, PR, and AR.

In a related embodiment, the specific glucocorticoid receptor antagonist binds to the glucocorticoid receptor with an association constant ($K_d$) that is at least 10-fold less than the $K_d$ for other nuclear receptors. In another embodiment, the specific glucocorticoid receptor antagonist binds to the glucocorticoid receptor with an association constant ($K_d$) that is at least 100-fold less than the $K_d$ for the other nuclear receptors. In another embodiment, the specific glucocorticoid receptor antagonist binds to the glucocorticoid receptor with an association constant ($K_d$) that is at least 1000-fold less than the $K_d$ for the other nuclear receptors.

Generally, treatment can be provided by administering an effective amount of a glucocorticoid receptor antagonist (GRA) of any chemical structure or mechanism of action and a glucocorticoid of any chemical structure or mechanism of action. Provided herein, are classes of exemplary GRAs and specific members of such classes. However, one of skill in the art will readily recognize other related or unrelated GRAs that can be employed in the treatment methods described herein.

1. GRAs Having a Steroidal Backbone

In some embodiments, an effective amount of a GRA with a steroidal backbone is administered to a subject for treatment of an ACTH-secreting tumor. Steroidal GRAs can be obtained by modification of the basic structure of glucocorticoid agonists, i.e., varied forms of the steroid backbone. The structure of cortisol can be modified in a variety of ways. The two most commonly known classes of structural modifications of the cortisol steroid backbone to create GRAs include modifications of the 11-β hydroxy group and modification of the 17-β side chain (See, e.g., Lefebvre, J. Steroid Biochem. 33:557-563, 1989).

Examples of steroidal GR antagonists include androgen-type steroidal compounds as described in U.S. Pat. No. 5,929,058, and the compounds disclosed in U.S. Pat. Nos. 4,296,206; 4,386,085; 4,447,424; 4,477,445; 4,519,946; 4,540,686; 4,547,493; 4,634,695; 4,634,696; 4,753,932; 4,774,236; 4,808,710; 4,814,327; 4,829,060; 4,861,763; 4,912,097; 4,921,638; 4,943,566; 4,954,490; 4,978,657; 5,006,518; 5,043,332; 5,064,822; 5,073,548; 5,089,488; 5,089,635; 5,093,507; 5,095,010; 5,095,129; 5,132,299; 5,166,146; 5,166,199; 5,173,405; 5,276,023; 5,380,839; 5,348,729; 5,426,102; 5,439,913; 5,616,458, 5,696,127, and 6,303,591. Such steroidal GR antagonists include cortexolone, dexamethasone-oxetanone, 19-nordeoxycorticosterone, 19-norprogesterone, cortisol-21-mesylate; dexamethasone-21-mesylate, 11β-(4-dimethylaminoethoxyphenyl)-17α-propynyl-17β-hydroxy-4,9-estradien-3-one (RU009), and (17α)-17-hydroxy-19-(4-methylphenyl)androsta-4,9(11)-dien-3-one (RU044).

Other examples of steroidal antiglucocorticoids are disclosed in Van Kampen et al. (2002) Eur. J. Pharmacol. 457(2-3):207, WO 03/043640, EP 0 683 172 B1, and EP 0 763 541 B1, each of which is incorporated herein by reference. EP 0 763 541 B1 and Hoyberg et al., Int'l J. of Neuro-psychopharmacology, 5:Supp. 1, S148 (2002); disclose the compound (11β,17β)-11-(1,3-benzodioxol-5-yl)-17-hydroxy-17-(1-propynyl)estra-4,9-dien-3-one (ORG 34517) which in one embodiment, is administered in an amount effective to treat an ACTH-secreting tumor in a subject.

2. Removal or Substitution of the 11-β Hydroxy Group

Glucocorticoid antagonists with modified steroidal backbones comprising removal or substitution of the 11-β hydroxy group are administered in one embodiment of the invention. This class includes natural GRAs, including cortexolone, progesterone and testosterone derivatives, and synthetic compositions, such as mifepristone (Lefebvre, et al. supra). Preferred embodiments of the invention include all 11-β aryl steroid backbone derivatives because, in some cases, these compounds can be devoid of progesterone receptor (PR) binding activity (Agarwal, FEBS 217:221-226, 1987). In another embodiment an 11-β phenyl-aminodimethyl steroid backbone derivative, which is both an effective anti-glucocorticoid and anti-progesterone agent, is administered. These compositions can act as reversibly-binding steroid receptor antagonists. For example, when bound to a 11-β phenyl-aminodimethyl steroid, the steroid receptor can be maintained in a conformation that cannot bind its natural ligand, such as cortisol in the case of GR (Cadepond, 1997, supra).

Synthetic 11-beta phenyl-aminodimethyl steroids include mifepristone, also known as RU486, or 17-β-hydrox-11-β-(4-dimethyl-aminophenyl)17-α-(1-propynyl)estra-4,9-dien-3-one). Mifepristone has been shown to be a powerful antagonist of both the progesterone and glucocorticoid (GR) receptors. Thus, in some embodiments, the GRA administered to treat an ACTH-secreting tumor is mifepristone, or a salt, tautomer, or derivative thereof. In other embodiments, however, administration of mifepristone is specifically excluded as a GRA for treatment of an ACTH-secreting tumor.

Another 11-β phenyl-aminodimethyl steroid shown to have GR antagonist effects includes the dimethyl aminoethoxyphenyl derivative RU009 (RU39.009), 11-β-(4-dimethyl-aminoethoxyphenyl)-17-α-(propynyl-17-β-hydroxy-4,9-estradien-3-one) (see Bocquel, J. Steroid Biochem. Molec. Biol. 45:205-215, 1993). Another GR antagonist related to RU486 is RU044 (RU43.044) 17-β-hydrox-17-α-19-(4-methyl-phenyl)-androsta-4,9(11)-dien-3-one) (Bocquel, 1993, supra). See also Teutsch, Steroids 38:651-665, 1981; U.S. Pat. Nos. 4,386,085 and 4,912,097.

One embodiment includes compositions that are irreversible anti-glucocorticoids. Such compounds include α-keto-methanesulfonate derivatives of cortisol, including cortisol-21-mesylate (4-pregnene-11-β, 17-α, 21-triol-3, 20-dione-21-methane-sulfonate and dexamethasone-21-mesylate (16-methyl-9-α-fluoro-1,4-pregnadiene-11 β, 17-α, 21-triol-3, 20-dione-21-methane-sulfonte). See Simons, J. Steroid Biochem. 24:25-32, 1986; Mercier, J. Steroid Biochem. 25:11-20, 1986; U.S. Pat. No. 4,296,206.

3. Modification of the 17-beta Side Chain Group

Steroidal anti-glucocorticoids which can be obtained by various structural modifications of the 17-β side chain are also used in the methods of the invention. This class includes synthetic antiglucocorticoids such as dexamethasone-oxetanone, various 17, 21-acetonide derivatives and 17-beta-carboxamide derivatives of dexamethasone (Lefebvre, 1989, supra; Rousseau, Nature 279:158-160, 1979).

4. Other Steroid Backbone Modifications

GRAs used in the various embodiments of the invention include any steroid backbone modification which effects a biological response resulting from a GR-agonist interaction. Steroid backbone antagonists can be any natural or synthetic variation of cortisol, such as adrenal steroids missing the C-19 methyl group, such as 19-nordeoxycorticosterone and 19-norprogesterone (Wynne, Endocrinology 107:1278-1280, 1980).

In general, the 11-βside chain substituent, and particularly the size of that substituent, can play a key role in determining the extent of a steroid's antiglucocorticoid activity. Substitutions in the A ring of the steroid backbone can also be important. For example, 17-hydroxypropenyl side chains can, in some cases, decrease antiglucocorticoid activity in comparison to 17-propynyl side chain containing compounds.

Additional glucocorticoid receptor antagonists known in the art and suitable for practice of the invention include 21-hydroxy-6,19-oxidoprogesterone (See Vicent, Mol. Pharm. 52:749-753, 1997), Org31710 (See Mizutani, J Steroid Biochem Mol Biol 42(7):695-704, 1992), RU43044, RU40555 (See Kim, J Steroid Biochem Mol Biol. 67(3):213-22, 1998), and RU28362.

5. Non-Steroidal Anti-Glucocorticoids as Antagonists

Non-steroidal glucocorticoid antagonists (GRAs) are also used in the methods of the invention to treat adrenal insufficiency in a subject. These include synthetic mimetics and analogs of proteins, including partially peptidic, pseudopeptidic and non-peptidic molecular entities. For example, oligomeric peptidomimetics useful in the invention include (α-β-unsaturated) peptidosulfonamides, N-substituted glycine derivatives, oligo carbamates, oligo urea peptidomimetics, hydrazinopeptides, oligosulfones and the like (See, e.g., Amour, Int. J. Pept. Protein Res. 43:297-304, 1994; de Bont, Bioorganic &Medicinal Chem. 4:667-672, 1996).

Examples of non-steroidal GR antagonists include the GR antagonist compounds disclosed in U.S. Pat. Nos. 5,696,127; 6,570,020; and 6,051,573; the GR antagonist compounds disclosed in US Patent Application 20020077356, the glucocorticoid receptor antagonists disclosed in Bradley et al., J. Med. Chem. 45, 2417-2424 (2002), e.g., 4α(S)-benzyl-2(R)-chloroethynyl-1,2,3,4,4α,9,10,10α(R)-octahydro-phenanthrene-2,7-diol ("CP 394531") and 4α(S)-benzyl-2(R)-prop-1-ynyl-1,2,3,4,4α,9,10,10α(R)-octahydro-phenanthrene-2,7-diol ("CP 409069"); and the compounds disclosed in PCT International Application No. WO 96/19458, which describes non-steroidal compounds which are high-affinity, highly selective antagonists for steroid receptors, such as 6-substituted-1,2-dihydro-N-protected-quinolines.

In some embodiments, adrenal insufficiency is treated with an effective amount of a non-steroidal GRA having a cyclohexyl-pyrimidine backbone, a fused azadecalin backbone, a heteroaryl ketone fused azadecalin backbone, or an octahydro fused azadecalin backbone. For example, adrenal insufficiency can be treated with effective amounts of one of the foregoing GRAs and a GC or a GC analog. Exemplary GRAs having a cyclohexyl-pyrimidine backbone include those described in U.S. Pat. No. 8,685,973. In some cases, the GRA having a cyclohexyl-pyrimidine backbone has the following structure:

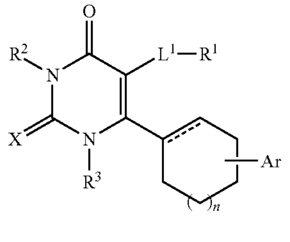

wherein the dashed line is absent or a bond;

X is selected from the group consisting of O and S;

$R^1$ is selected from the group consisting of cycloalkyl, heterocycloalkyl, aryl and heteroaryl, optionally substituted with from 1 to 3 $R^{1a}$ groups;

each $R^{1a}$ is independently selected from the group consisting of H, $C_{1-6}$ alkyl, $C_{2-6}$ alkenyl, $C_{2-6}$ alkynyl, $C_{1-6}$ alkoxy, $C_{1-6}$ alkyl-$OR^{1b}$, halogen, $C_{1-6}$ haloalkyl, $C_{1-6}$ haloaloxy, —$OR^1$, —$NR^{1b}R^{1c}$, —$C(O)R^{1b}$, —$C(O)OR^{1b}$, —$OC(O)R^{1b}$, —$C(O)NR^{1b}R^{1c}$, —$NR^{1b}C(O)R^{1c}$, —$SO_2R^{1b}$, —$SO_2NR^{1b}R^{1c}$, cycloalkyl, heterocycloalkyl, aryl and heteroaryl;

$R^{1b}$ and $R^{1c}$ are each independently selected from the group consisting of H and $C_{1-6}$ alkyl;

$R^2$ is selected from the group consisting of H, $C_{1-6}$ alkyl, $C_{1-6}$ alkyl-$OR^{1b}$, $C_{1-6}$ alkyl-$NR^{1b}R^{1c}$ and $C_{1-6}$ alkylene-heterocycloalkyl;

$R^3$ is selected from the group consisting of H and $C_{1-6}$ alkyl;

Ar is aryl, optionally substituted with 1-4 $R^4$ groups;

each $R^4$ is independently selected from the group consisting of H, $C_{1-6}$ alkyl, $C_{1-6}$ alkoxy, halogen, $C_{1-6}$ haloalkyl and $C_{1-6}$ haloalkoxy;

$L^1$ is a bond or $C_{1-6}$ alkylene; and subscript n is an integer from 0 to 3, or a salts and isomers thereof.

Exemplary GRAs having a fused azadecalin backbone include those described in U.S. Pat. Nos. 7,928,237; and 8,461,172. In some cases, the GRA having a fused azadecalin backbone has the following structure:

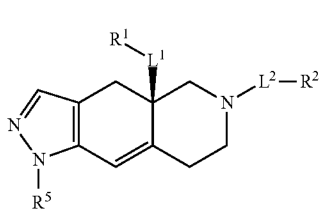

wherein $L^1$ and $L^2$ are members independently selected from a bond and unsubstituted alkylene;

$R^1$ is a member selected from unsubstituted alkyl, unsubstituted heteroalkyl, unsubstituted heterocycloalkyl, —$OR^{1A}$, $NR^{1C}R^{1D}$, —$C(O)NR^{1C}R^{1D}$ and —$C(O)OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;

$R^2$ has the formula:

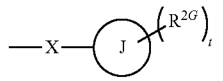

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$;

J is phenyl;

t is an integer from 0 to 5;

X is —$S(O_2)$—; and $R^5$ is phenyl optionally substituted with 1-5 $R^{5A}$ groups, wherein $R^{5A}$ is a member selected from hydrogen, halogen, —$OR^{5A1}$, —$S(O_2)NR^{5A2}R^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and isomers thereof.

Exemplary GRAs having a heteroaryl ketone fused azadecalin backbone include those described in U.S. 2014/0038926. In some cases, the GRA having a heteroaryl ketone fused azadecalin backbone has the following structure:

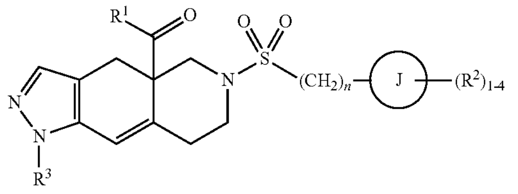

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, and $C_{3-8}$ heterocycloalkyl;

ring J is selected from the group consisting of a cycloalkyl ring, a heterocycloalkyl ring, an aryl ring and a heteroaryl ring, wherein the heterocycloalkyl and heteroaryl rings have from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl, wherein the heterocycloalkyl groups are optionally substituted with 1-4 $R^{2c}$ groups;

alternatively, two $R^2$ groups linked to the same carbon are combined to form an oxo group (=O);

alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and $C_{1-6}$ alkyl;

each $R^{2c}$ is independently selected from the group consisting of hydrogen, halogen, hydroxy, $C_{1-6}$ alkoxy, $C_{1-6}$ haloalkoxy, —CN, and —$NR^{2a}R^{2b}$;

each $R^{2d}$ is independently selected from the group consisting of hydrogen and $C_{1-6}$ alkyl, or two $R^{2d}$ groups attached to the same ring atom are combined to form (=O);

$R^3$ is selected from the group consisting of phenyl and pyridyl, each optionally substituted with 1-4 $R^{3a}$ groups;

each $R^{3a}$ is independently selected from the group consisting of hydrogen, halogen, and $C_{1-6}$ haloalkyl; and subscript n is an integer from 0 to 3;

or salts and isomers thereof.

Exemplary GRAs having an octohydro fused azadecalin backbone include those described in U.S. Provisional Patent Appl. No. 61/908,333, entitled Octahydro Fused Azadecalin Glucocorticoid Receptor Modulators, filed on Nov. 25, 2013. In some cases, the GRA having an octohydro fused azadecalin backbone has the following structure:

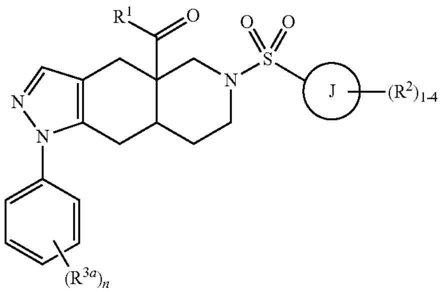

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, N-oxide, and $C_{3-8}$ cycloalkyl;

ring J is selected from the group consisting of an aryl ring and a heteroaryl ring having from 5 to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2R^{2a}$, $C_{3-8}$ cycloalkyl, and $C_{3-8}$ heterocycloalkyl having from 1 to 3 heteroatoms each independently selected from the group consisting of N, O and S;

alternatively, two $R^2$ groups on adjacent ring atoms are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2c}$ groups;

$R^{2a}$, $R^{2b}$ and $R^{2c}$ are each independently selected from the group consisting of hydrogen and $C_{1-6}$ alkyl;

each $R^{3a}$ is independently halogen; and subscript n is an integer from 0 to 3;

or salts and isomers thereof.

C. Glucocorticoids

The methods of the present invention generally include administering a glucocorticoid, a synthetic glucocorticoid or a functional derivative thereof. A glucocorticoid includes any chemical compound that can bind to and activate the glucocorticoid receptor. In some embodiments, the synthetic glucocorticoid is hydrocortisone, prednisone, prednisolone, dexamethasone, a glucocorticoid analogue, a synthetic glucocorticoid analogue, derivatives thereof, or any combination thereof.

Non-limiting examples of synthetic glucocorticoids that can be used in the present invention include beclomethasone dipropionate, betamethasone, betamethasone acetate, betamethasone benzoate, betamethasone disodium phosphate, cortisone acetate, dexamethasone, dexamethasone sodium phosphate, fludrocortisone acetate, flunisolide, fluoncinolone acetonide, fluocinonide, flurandrenolide, deflazacort, methylprednisolone, methylprednisolone acetate, methylprednisolone sodium succinnate, prednisolone, prednisolone acetate, prednisolone sodium phosphate, prednisolone tebutate, prednisone, triamcinolone, triamcinolone acetonide, triamcinolone diacetate and triamcinolone hexaacetonide, including pharmaceutically acceptable esters, salts and complexes thereof.

In some embodiments, the present invention provides a pharmaceutical composition including a compound of the present invention and a pharmaceutically acceptable excipient. In some embodiments, the present invention provides a pharmaceutical composition including a glucocorticoid receptor antagonist of the present invention and a pharmaceutically acceptable excipient. In some embodiments, the present invention provides a pharmaceutical composition including a glucocorticoid of the present invention and a pharmaceutically acceptable excipient. In some embodiments, the present invention provides a pharmaceutical composition including a glucocorticoid receptor antagonist and a glucocorticoid of the present invention and a pharmaceutically acceptable excipient.

D. Pharmaceutical Compositions of Glucocorticoid Receptor Antagonists and Glucocorticoids The GRA and/or GC compositions of the present invention can be prepared in a wide variety of oral, parenteral and topical dosage forms. Oral preparations of either include tablets, pills, powder, dragees, capsules, liquids, lozenges, cachets, gels, syrups, slurries, suspensions, etc., suitable for ingestion by the patient. The GRA and/or GC compositions of the present invention can also be administered by injection, that is, intravenously, intramuscularly, intracutaneously, subcutaneously, intraduodenally, or intraperitoneally. Also, the GRA and/or GC compositions described herein can be administered by inhalation, for example, intranasally. Additionally, the GRA and/or GC compositions of the present invention can be administered transdermally. The GRA and/or GC compositions of this invention can also be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention provides pharmaceutical compositions of a GRA including a pharmaceutically acceptable carrier or excipient and a GRA compound of the present invention. The present invention provides pharmaceutical compositions of a GC including a pharmaceutically acceptable carrier or excipient and a GC compound of the present invention.

For preparing pharmaceutical compositions from the GRA or GC compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving one or more compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The GRA and/or GC compositions of the present invention can also be delivered as microspheres for slow release in the body. For example, microspheres can be formulated for administration via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months.

In another embodiment, the GRA and/or GC compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These GRA and/or GC formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the GRA and/or GC formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

The GRA and/or GC composition can also contain other compatible therapeutic agents. The compounds described herein can be used in combination with one another, with other active agents known to be useful in antagonizing a glucocorticoid receptor, or with adjunctive agents that may not be effective alone, but may contribute to the efficacy of the active agent.

E. Methods of Administration

The GRA and/or GC compounds or compositions of the present invention can be delivered by any suitable means, including oral, parenteral (e.g., intravenous injection or intramuscular injection) and topical methods. Transdermal administration methods, by a topical route, can be formulated as applicator sticks, solutions, suspensions, emulsions, gels, creams, ointments, pastes, jellies, paints, powders, and aerosols. Accordingly, the GC compounds described herein can be administered in an oral dosage form or an injection dosage form.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

GRAs can be administered orally. For example, the GRA can be administered as a pill, a capsule, or liquid formulation as described herein. Alternatively, GRAs can be provided via parenteral administration. For example, the GRA can be administered intravenously (e.g., by injection or infusion). Similarly, the GC can be administered orally, e.g., as a pill, a capsule or liquid formulation. Alternatively, the GC can be administered via parenteral administration, e.g., intravenously. Additional methods of administration of the compounds described herein, and pharmaceutical compositions or formulations thereof, are described below.

The GRA and GC compounds and compositions of the present invention can be co-administered. Co-administration includes administering the GRA compound or composition of the present invention within 0.5, 1, 2, 4, 6, 8, 10, 12, 16, 20, or 24 hours of the GC compound or composition of the present invention. Co-administration also includes administering simultaneously, approximately simultaneously (e.g., within about 1, 5, 10, 15, 20, or 30 minutes of each other), or sequentially in any order. Moreover, the compounds and compositions of the present invention can each be administered once a day, or two, three, or more times per day so as to provide the preferred dosage level per day.

In some embodiments, co-administration can be accomplished by co-formulation, i.e., preparing a single pharmaceutical composition including the compounds and compositions of the present invention and any other agent. Alternatively, the various components can be formulated separately.

Secondary adrenal insufficiency can be treated in a subject in need thereof, by simultaneously or sequentially administering to the subject i) a glucocorticoid receptor antagonist (GRA); and ii) glucocorticoid (GC), in effective amounts such that the patient's morning plasma cortisol level is at least 12 μg/dL. The GRA and GC can be administered in a single (i.e., combined) dose form, or as a GRA dose and a GC dose. The GRA can be administered first, followed by a second administration of the GC. Alternatively, the GC can be administered first, followed by a second administration of the GRA.

Glucocorticoid receptor antagonists (GRAs) can be administered simultaneously or sequentially with a glucocorticoid (e.g., glucocorticoid or an analog thereof) at a dose of from about 0.1 mg to about 10,000 mg, about 1 mg to about 1000 mg, about 10 mg to about 750 mg, about 25 mg to about 500 mg, about 50 mg to about 250 mg, or about 75 mg to about 150 mg of the GRA. In some cases, GRAs can be administered simultaneously or sequentially with a glucocorticoid (e.g., glucocorticoid or an analog thereof) at a dose of about 1, 5, 10, 20, 30, 40, 50, 60, 70, 80, 90, 100, 200, 300, 400, 500, 600, 700, 800, 900 or 1000 mg of the GRA. In some cases, GRAs can be administered simultaneously or sequentially with a glucocorticoid (e.g., glucocorticoid or an analog thereof) at a dose of about 0.1, 0.25, 0.5, 0.75, 1, 1.5, 2, 2.5, 3, 4, 5, 10, 15, 20, 25, 50, 75, 100, 125, or 150 mg/kg of the GRA. In other cases, one or more of the foregoing GRA dosages or a dose within one of the foregoing GRA dose ranges can be administered about four times per day, three times per day, once per day, semi-weekly, weekly, bi-weekly, or monthly. In yet other cases, a subject is administered a high dose (e.g., 500 mg or more) of GRA for a period of time (e.g., twice per day for one week) and then administered a low dose (e.g., 100 mg or less) of GRA for a period of time. Alternatively, a subject can be administered a low dose (e.g., 150 mg or less) of GRA for a period of time (e.g., every other day for one week or more) and then administered a high dose (e.g., 600 mg or more) of GRA for a period of time (e.g., daily). For example, the treatment course of the GRA can follow the schedule of: a) 150 mg every other day for two months, b) 300 mg every other day for one month, c) 300 mg daily for one month, d) 600 mg daily for three months, and e) 300 mg every other day for two months.

Glucocorticoids (e.g., glucocorticoid or an GC) can be administered simultaneously or sequentially with a GRA at a dose of from about 0.1 mg to about 10,000 mg, about 1 mg to about 1000 mg, about 10 mg to about 750 mg, about 25 mg to about 500 mg, about 50 mg to about 250 mg, or about 75 mg to about 150 mg of the glucocorticoid. In some cases, the glucocorticoid can be administered simultaneously or sequentially with a GRA at a dose of about 1, 5, 10, 20, 30, 40, 50, 60, 70, 80, 90, 100, 200, 300, 400, 500, 600, 700, 800, 900 or 1000 mg of the glucocorticoid. In other cases, glucocorticoid can be administered simultaneously or sequentially with a GRA at a dose of about 0.1, 0.25, 0.5, 0.75, 1, 1.5, 2, 2.5, 3, 4, 5, 10, 15, 20, 25, 50, 75, 100, 125, or 150 mg/kg of the glucocorticoid. In some embodiments, one or more of the foregoing dosages of glucocorticoid or a dose within one of the foregoing dose ranges of glucocorticoid can be administered about four times per day, three times per day, once per day, semi-weekly, weekly, bi-weekly, or monthly. The effective amount of unit dose can be about 0.25 mg, 0.5 mg, 1.0 mg, 2.0 mg, 5.0 mg, 10 mg, 20 mg and 30 mg per unit dosage.

In some cases, a subject is administered a high dose (e.g., 30 mg or more) of glucocorticoid for a period of time (e.g., twice per day for one week) and then administered a low dose (e.g., 10 mg or less) of glucocorticoid for a period of time. In yet other cases, a subject is administered a low dose (e.g., 10 mg or less) of glucocorticoid for a period of time (e.g., twice per day for one week) and then administered a high dose (e.g., 30 mg or more) of glucocorticoid for a period of time. For example, the treatment course of hydrocortisone can follow the schedule of: a) 15 mg daily for 5 months, and b) 10 mg daily for one month.

The dosage schedule and amounts effective for this use, i.e., the "dosing regimen," will depend upon a variety of factors, including the severity of the disease, the disease etiology, the patient's physical status, age and the like. In calculating the dosage regimen for a patient, the mode of administration also is taken into consideration. The dosage regimen also takes into consideration pharmacokinetics parameters well known in the art, i.e., the GRA's and/or GC's rate of absorption, bioavailability, metabolism, clearance, and the like (see, e.g., Hidalgo-Aragones, J. Steroid Biochem. Mol. Biol. 58:611-617, 1996; Groning, Pharmazie 51:337-341, 1996; Fotherby, Contraception 54:59-69, 1996; Johnson, J. Pharm. Sci. 84:1144-1146, 1995; Rohatagi, Pharmazie 50:610-613, 1995; Brophy, Eur. J. Clin. Pharmacol. 24:103-108, 1983; Remington's Pharmaceutical Science, supra).

F. Methods of Determining Treatment Efficacy

Any one or more of the foregoing detection methods described herein, or known generally in the art, can be used to assess the efficacy of the treatment. In some embodiments, a subject with secondary adrenal insufficiency is treated by administering effective amounts of a GRA and a GC that increase the subject's morning cortisol level, e.g., basal cortisol level to at least 12 μg/dL, and the treatment can be monitored to determined its efficacy. For example, efficacy can be indicated by detecting the level of plasma, serum, urine, or saliva basal cortisol, e.g., basal total or free cortisol. In some embodiments, co-administration of a therapeutically effective amount of a GC and a therapeutically effective amount of a GRA affects the patient's basal plasma cortisol level such that it is 12 μg/dL or higher, or a comparable level in another biological sample. In other embodiments, co-administration of a therapeutically effective amount of a GC and a therapeutically effective amount of a GRA changes the patient's basal serum cortisol level such that the level is 12 μg/dL or higher, or a comparable level in another biological sample.

As described above, an individual's cortisol level is regulated by ACTH which is synthesized in the pituitary in response to corticotropin releasing hormone (CRH) from the hypothalamus. Cortisol is mostly found bound to glucocorticoid-binding globulin and albumin. Free circulating, unbound cortisol is the physiologically active form and is <5% of total cortisol. Without being bound to any particular therapy, co-administration of a glucocorticoid and a glucocorticoid receptor antagonist can stimulate an individual to secrete cortisol in the morning.

Cortisol levels can be measured in serum, plasma, saliva, feces or urine using assays, including but not limited to, immunoassays, competitive immunoassays, mass spectrometry, e.g., liquid chromatography-tandem mass spectrometry (LC/MS-MS) or tandem mass spectrometry (MS-MS). In some embodiments, the level of total or free cortisol in serum, plasma, saliva, urine or feces is determined using an immunoassay such as, but not limited to, the ADVIA Centaur® Cortisol assay (Siemens Healthcare Global), ARCHITECT i2000SR cortisol (Abbott), Immulite® 2000 Cortisol assay (Siemans Healthcare Global; #L2KCO2), Vitros® ECi Cortisol assay (Ortho Clinical Diagnostics; #107 4053), and Elecsys® Cortisol Immunoassay (Roche Molecular Diagnostics; #11875116160). One of ordinary skill in the art will recognize that any method for detecting cortisol levels in a biological sample taken from a subject, e.g., human subject can be used.

G. Kits

The present invention provides kits. The kits comprise daily doses of the GRA and GC and in some cases, a biological sample collecting device. In some embodiments, the kit also includes any other component necessary to perform the methods described herein, such as a container, instructions for drug administration, and instructions for sample collection.

In some cases, a patient's plasma is collected by any known plasma collection device. Some plasma collection devices useful in the present invention include, but are not limited to, vacutainers. The plasma collection devices can optionally comprise additives in the device, such as anticoagulants (EDTA, sodium citrate, heparin, oxalate), a gel with intermediate density between blood cells and blood plasma, particles causing the blood to clot, a gel to separate blood cells from serum, thrombin and fluoride, among others.

III. Examples

Example 1: Case Report of Treating a Female Patient Suffering from Secondary Adrenal Insufficiency with a Glucocorticoid and a Glucocorticoid Receptor Antagonist The patient is a 39 year old woman who developed depression at the age of 20 for which she was placed on various psychotropic medications. At age 28, she developed progressive malaise, 25 pound weight gain, muscle weakness, easing bruising, hypertension and foot stress fracture. At age 31, she underwent screening DEXA bone density scan because of her personal history of fracture and a family history of advanced osteoporosis and genetically confirmed hypophosphatasia in her mother. The DEXA bone density scan disclosed a T-score of −3.4 at the lumbar spine and −3.1 at the hip. DNA sequencing of the ALPL (alkaline phosphatase, liver/bone/kidney) gene revealed no detectable disease-causing mutations. Further testing for secondary causes of osteoporosis included 24-hour urinary free cortisol which was markedly elevated at 499 mcg/day (range 10-80 mcg/day). Plasma ACTH level was undetectable. Adrenal imaging revealed a 3-cm right adrenal mass. At age 33, she underwent uncomplicated right laparoscopic adrenalactomy and histopathology confirmed a 3.7 cm adrenal cortical adenoma. The patient underwent a unilateral procedure, leaving one adrenal gland intact.

Post-operatively the patient was placed on hydrocortisone replacement, initially at a dose of 40 mg/day given in divided doses and gradually tapered to 30 mg/day over the following several months. One year after her adrenalectomy, her hydrocortisone had been further tapered to 15 mg/day, which remained her maintenance dose.

During the ensuing 6 years after her adrenalectomy, the patient generally felt unwell with symptoms of episodic nausea, headaches, lightheadedness, mood swings and generalized weakness. Quarterly measurement of serum cortisol and plasma ACTH levels (performed after holding hydrocortisone for 18 hours) consistently yielded undetectable values for both parameters. During this 6 year period, she had one pregnancy, occurring 3 years after adrenalectomy and progressing to full-term delivery of a healthy boy. She had two other hospitalizations (separated by 4 years) for near-syncope, malaise, nausea and vomiting (but without hypoglycemia or hypotension). Both episodes were treated with 48-hours of intravenous stress-doses of glucocorticoids and saline, followed by improvement of her symptoms and subsequent tapering of glucocorticoids to a replacement dose of hydrocortisone 15 mg/day.

The failure of the HPA axis to recover six years after adrenalectomy (despite physiological steroid dosing) prompted magnetic resonance imaging of the sella to rule out structural abnormalities of the hypothalamus, infundibulum and pituitary. This MRI was unremarkable. At that time, after a balanced discussion of risk and benefit, mifepristone 150 mg every other day was initiated and the dose of hydrocortisone 15 mg/day was continued. Over the ensuing five months, the dose of mifepristone was gradually escalated to 300 mg every other day, then 300 mg daily and finally maintained at 600 mg daily. During this time, rapid recovery of the HPA axis was noted (initially with a rise in ACTH into the supra-normal range 4-months after starting mifepristone, followed by a subsequent rise in cortisol levels). The dose of hydrocortisone was lowered and ultimately stopped 8 months after initiation of mifepristone. The patient tolerated mifepristone remarkably well; with the only side effects being amenorrhea and pruritis (she had a preexisting history of urticaria). The pruritis was tolerable and managed with over the counter anti-histamines. At no point during treatment with mifepristone did the patient develop signs or symptoms of adrenal insufficiency. Her menses returned 3 weeks after discontinuation of mifepristone. Table 1 summarizes recovery of the HPA axis after initiation of mifepristone.

TABLE 1

| Drug Dosing Schedule and Response | | | | | | | | | |
|---|---|---|---|---|---|---|---|---|---|
| Month | 0 | 1 | 3 | 4 | 5 | 6 | 8 | 10 | 11 |
| Mife dose (mg) | 0 | 150 TIW | 300 TIW | 300 daily | 600 daily | 600 daily | 300 TIW | 0 | 0 |
| HC dose (mg) | 15 | 15 | 15 | 15 | 15 | 10 | 0 | 0 | 0 |
| ACTH (pg/mL) | 5 | 15 | 18 | 60 | 78 | 173 | 126 | 26 | 45 |
| Cortisol (ug/dL) | <1 | <1 | <1 | 3.6 | 4.6 | 10.5 | 13.6 | 13.5 | 15.3 |
| DHEA (ng/ml) | <0.05 | <0.05 | <0.05 | <0.05 | <0.05 | <0.05 | <0.05 | <0.05 | 0.053 |

"Mife" denotes mifepristone.
"HC" denotes hydrocortisone.
"TIW" denotes three times per week.

This example illustrates that a patient with second adrenal insufficiency was successfully treated by co-administration of hydrocortisone and mifepristone. Recovery of the patient's HPA axis was achieved. The patient's ACTH and cortisol levels increased in response to the drug treatment. Normal levels of ACTH and cortisol were maintained after completion of the treatment.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. All publications, patents, and patent applications cited herein are hereby incorporated by reference in their entirety for all purposes.

What is claimed is:

1. A method of treating secondary adrenal insufficiency, the method comprising co-administering a therapeutically effective amount of a glucocorticoid (GC) and a non-steroidal glucocorticoid receptor antagonist (GRA), wherein the glucocorticoid receptor antagonist backbone is a fused azadecalin, to a patient in need thereof, wherein administering said non-steroidal GRA comprises administering initial low dose amounts of the non-steroidal GRA once per day along with initial high dose amounts of said GC administration for at least a week, wherein said once-daily initial low dose amount said non-steroidal GRA is between 100 milligrams (mg) and 150 mg of the non-steroidal GRA, and wherein said initial high dose amount of said GC is between 15 and 30 mg of the GC, and then continuing to administer the GC and continuing to administer the non-steroidal GRA once per day, wherein said continued once per day non-steroidal GRA administration is at a non-steroidal GRA dose amount that is greater than said initial GRA low dose amount, and wherein said continued GC administration is at a GC dose amount that is less than said initial GC high dose amount, effective to increase the patient's morning plasma levels of cortisol to at least about 12 μg/dL, whereby said secondary adrenal insufficiency is treated, wherein the glucocorticoid receptor antagonist backbone is a fused azadecalin.

2. The method of claim 1, wherein the fused azadecalin is a compound having the following formula:

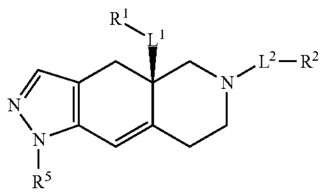

wherein $L^1$ and $L^2$ are members independently selected from a bond and unsubstituted alkylene;

$R^1$ is a member selected from unsubstituted alkyl, unsubstituted heteroalkyl, unsubstituted heterocycloalkyl, —$OR^{1A}$ $N^{1C}R^{1D}$, —$C(O)NR^{1C}R^{1D}$ and —$C(O)OR^{1A}$, wherein $R^{1A}$ is a member selected from hydrogen, unsubstituted alkyl and unsubstituted heteroalkyl, $R^{1C}$ and $R^{1D}$ are members independently selected from unsubstituted alkyl and unsubstituted heteroalkyl, wherein $R^{1C}$ and $R^{1D}$ are optionally joined to form an unsubstituted ring with the nitrogen to which they are attached, wherein said ring optionally comprises an additional ring nitrogen;

$R^2$ has the formula:

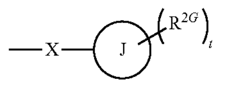

wherein $R^{2G}$ is a member selected from hydrogen, halogen, unsubstituted alkyl, unsubstituted heteroalkyl, unsubstituted cycloalkyl, unsubstituted heterocycloalkyl, —CN, and —$CF_3$;

J is phenyl;

t is an integer from 0 to 5;

X is —$S(O_2)$—; and $R^5$ is phenyl optionally substituted with 1-5 $R^{5A}$ groups, wherein $R^{5A}$ is a member selected from hydrogen, halogen, —$OR^{5A1}$, $S(O_2)NR^{5A2}R^{5A3}$, —CN, and unsubstituted alkyl, wherein $R^{5A1}$ is a member selected from hydrogen and unsubstituted alkyl, and $R^{5A2}$ and $R^{5A3}$ are members independently selected from hydrogen and unsubstituted alkyl, or salts and thereof.

3. The method of claim 1, wherein the patient has secondary adrenal insufficiency after successful surgery for endogenous Cushing's syndrome.

4. The method of claim 1, wherein the patient has secondary adrenal insufficiency after successful surgery of a pituitary ACTH-secreting tumor, an extra-adrenal cortisol secreting tumor, a unilateral hyperplastic adrenal gland associated with autonomous cortisol secretion, an ectopic ACTH secreting non-pituitary tumor, or a unilateral adrenocortical cortisol secreting tumor.

5. The method of claim 1, wherein the patient has not received glucocorticoid and glucocorticoid receptor antagonist treatment.

6. The method of claim 5, wherein the patient has not been treated for a disorder or condition selected from the group consisting of glaucoma, inflammatory diseases, rheumatoid arthritis, asthma and rhinitis, chronic pulmonary disease, allergies, and autoimmune diseases.

7. The method of claim 5, wherein the patient has not been treated to reduce a side effect of glucocorticoid treatment.

8. The method of claim 7, wherein the side effect is selected from the group consisting of weight gain, glaucoma, fluid retention, increased blood pressure, mood swings, cataracts, high blood sugar, diabetes, infection, loss of calcium from bones, osteoporosis, menstrual irregularities, fat redistribution, growth retardation, and cushingoid appearance.

9. The method of claim 1, wherein the glucocorticoid is selected from the group consisting of hydroxycortisone, prednisone and dexamethasone.

* * * * *